(12) United States Patent
Himmelsbach et al.

(10) Patent No.: US 7,645,763 B2
(45) Date of Patent: Jan. 12, 2010

(54) 8-[3-AMINO-PIPERIDIN-1-YL]-XANTHINES, THEIR PREPARATION AND THEIR USE AS PHARMACEUTICAL COMPOSITION

(75) Inventors: Frank Himmelsbach, Mittelbiberach (DE); Elke Langkopf, Warthausen (DE); Matthias Eckhardt, Biberach (DE); Mohammad Tadayyon, Ulm (DE); Leo Thomas, Biberach (DE)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 596 days.

(21) Appl. No.: 11/062,518

(22) Filed: Feb. 22, 2005

(65) Prior Publication Data

US 2005/0187227 A1 Aug. 25, 2005

Related U.S. Application Data

(60) Provisional application No. 60/551,752, filed on Mar. 10, 2004.

(30) Foreign Application Priority Data

Feb. 23, 2004 (DE) ........................ 10 2004 009 039

(51) Int. Cl.
C07D 473/06 (2006.01)
C07D 519/00 (2006.01)
A61K 31/522 (2006.01)
A61P 3/10 (2006.01)
A61P 3/04 (2006.01)

(52) U.S. Cl. ............................ 514/263.21; 514/263.22; 514/263.23; 514/263.24; 514/263.34; 514/263.36; 544/268; 544/269; 544/270; 544/272

(58) Field of Classification Search ............... 514/263.2, 514/263.21, 263.22, 263.23, 263.34, 263.36, 514/263.24; 544/268, 269, 270, 272
See application file for complete search history.

(56) References Cited

U.S. PATENT DOCUMENTS

| | | | |
|---|---|---|---|
| 2,928,833 A | 3/1960 | Leake et al. | |
| 4,005,208 A | 1/1977 | Bender | |
| 4,599,338 A | 7/1986 | Regnier et al. | |
| 5,041,448 A | 8/1991 | Janssens | |
| 5,051,517 A | 9/1991 | Findeisen | |
| 5,223,499 A | 6/1993 | Greenlee | |
| 5,234,897 A | 8/1993 | Findeisen et al. | |
| 5,258,380 A | 11/1993 | Janssens | |
| 5,266,555 A | 11/1993 | Findeisen et al. | |
| 5,389,642 A | 2/1995 | Dorsch | |
| 5,470,579 A | 11/1995 | Bonte et al. | |
| 5,719,279 A | 2/1998 | Kuefner-Muhl et al. | |
| 5,753,635 A | 5/1998 | Buckman | |
| 6,004,950 A * | 12/1999 | Friesen et al. ............... | 514/183 |
| 6,303,661 B1 | 10/2001 | Demuth | |
| 6,342,601 B1 | 1/2002 | Bantick | |
| 6,548,481 B1 | 4/2003 | Demuth et al. | |
| 6,579,868 B1 | 6/2003 | Asano | |
| 6,784,195 B2 | 8/2004 | Hale et al. | |
| 6,821,978 B2 | 11/2004 | Chackalamannil | |
| 6,869,947 B2 | 3/2005 | Kanstrup | |
| 7,060,722 B2 | 6/2006 | Kitajima | |
| 7,074,794 B2 | 7/2006 | Kitajima | |
| 7,074,798 B2 | 7/2006 | Yoshikawa | |
| 7,074,923 B2 | 7/2006 | Dahanukar | |
| 7,109,192 B2 | 9/2006 | Hauel | |
| 7,179,809 B2 | 2/2007 | Eckhardt | |
| 7,183,280 B2 * | 2/2007 | Himmelsbach et al. ..... | 514/248 |
| 7,192,952 B2 | 3/2007 | Kanstrup | |
| 7,217,711 B2 | 5/2007 | Eckhardt | |
| 7,235,538 B2 | 6/2007 | Kanstrup et al. | |
| 7,294,636 B2 * | 11/2007 | Cumming et al. ........... | 514/304 |
| 7,407,955 B2 * | 8/2008 | Himmelsbach et al. .. | 514/234.2 |
| 7,482,337 B2 * | 1/2009 | Himmelsbach et al. | 514/211.09 |
| 2002/0161001 A1 | 10/2002 | Kanstrup | |
| 2002/0169174 A1 | 11/2002 | Chackalamannil et al. | |
| 2002/0198205 A1 | 12/2002 | Himmelsbach | |
| 2003/0105077 A1 | 6/2003 | Kanstrup et al. | |
| 2003/0199528 A1 | 10/2003 | Kanstrup | |
| 2003/0232987 A1 | 12/2003 | Dahanukar et al. | |
| 2003/0236272 A1 | 12/2003 | Carr | |
| 2004/0034014 A1 | 2/2004 | Kanstrup et al. | |

(Continued)

FOREIGN PATENT DOCUMENTS

CA 2136288 A1 5/1995

(Continued)

OTHER PUBLICATIONS

Busso et al., American Journal of Pathology 166:433-442 (2005).*

(Continued)

*Primary Examiner*—Mark L Berch
(74) *Attorney, Agent, or Firm*—Michael P. Morris; Mary-Ellen M. Devlin; David L. Kershner

(57) ABSTRACT

The present invention relates to substituted xanthines of general formula

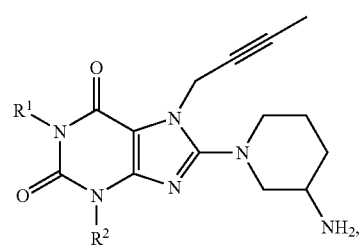

(I)

wherein $R^1$ and $R^2$ are defined as in the claims, the tautomers, the stereoisomers, the mixtures thereof, and the salts thereof, which have valuable pharmacological properties, particularly an inhibiting effect on the activity of the enzyme dipeptidylpeptidase-IV (DPP-IV).

9 Claims, No Drawings

U.S. PATENT DOCUMENTS

| | | | |
|---|---|---|---|
| 2004/0077645 A1 | 4/2004 | Himmelsbach et al. | |
| 2004/0082570 A1 | 4/2004 | Yoshikawa | |
| 2004/0087587 A1 | 5/2004 | Himmelsbach | |
| 2004/0097510 A1* | 5/2004 | Himmelsbach et al. | 514/248 |
| 2004/0116328 A1 | 6/2004 | Yoshikawa et al. | |
| 2004/0122228 A1 | 6/2004 | Maier | |
| 2004/0138214 A1* | 7/2004 | Himmelsbach et al. | 514/230.5 |
| 2004/0138215 A1 | 7/2004 | Eckhardt | |
| 2004/0166125 A1 | 8/2004 | Himmelsbach | |
| 2005/0020574 A1 | 1/2005 | Hauel et al. | |
| 2005/0026921 A1 | 2/2005 | Eckhardt | |
| 2005/0130985 A1 | 6/2005 | Himmelsbach | |
| 2005/0171093 A1 | 8/2005 | Eckhardt et al. | |
| 2005/0203095 A1 | 9/2005 | Eckhardt | |
| 2005/0234108 A1* | 10/2005 | Himmelsbach et al. | 514/345 |
| 2005/0261352 A1 | 11/2005 | Eckhardt | |
| 2006/0004074 A1 | 1/2006 | Eckhardt | |
| 2006/0058323 A1* | 3/2006 | Eckhardt et al. | 514/263.22 |
| 2006/0063787 A1 | 3/2006 | Yoshikawa | |
| 2006/0079541 A1 | 4/2006 | Langkopf | |
| 2006/0094722 A1 | 5/2006 | Yasuda | |
| 2006/0100199 A1 | 5/2006 | Yoshikawa et al. | |
| 2006/0142310 A1* | 6/2006 | Pfrengle et al. | 514/263.22 |
| 2006/0173056 A1 | 8/2006 | Kitajima | |
| 2006/0205711 A1 | 9/2006 | Himmelsbach | |
| 2006/0205737 A1* | 9/2006 | Becker et al. | 514/255.03 |
| 2006/0205769 A1* | 9/2006 | Brown et al. | 514/304 |
| 2006/0205943 A1* | 9/2006 | Dahanukar et al. | 544/267 |
| 2006/0247226 A1 | 11/2006 | Himmelsbach | |
| 2007/0027168 A1* | 2/2007 | Pfrengle et al. | 514/263.22 |
| 2007/0088038 A1 | 4/2007 | Eckhardt | |
| 2007/0093659 A1 | 4/2007 | Bonfanti | |
| 2007/0142383 A1 | 6/2007 | Eckhardt | |
| 2007/0185091 A1 | 8/2007 | Himmelsbach et al. | |
| 2007/0219178 A1 | 9/2007 | Muramoto | |
| 2007/0259900 A1 | 11/2007 | Sieger | |
| 2007/0281940 A1 | 12/2007 | Dugi | |
| 2008/0214868 A1* | 9/2008 | Rebiere et al. | 564/162 |
| 2008/0249089 A1* | 10/2008 | Himmelsbach et al. | 514/234.2 |
| 2008/0255159 A1* | 10/2008 | Himmelsbach et al. | 514/263.22 |

FOREIGN PATENT DOCUMENTS

| | | |
|---|---|---|
| CA | 2418656 A1 | 2/2002 |
| CA | 2496325 A1 | 3/2004 |
| CA | 2496249 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2590912 A1 | 6/2006 |
| DE | 10109021 A1 | 9/2002 |
| DE | 10117803 A1 | 10/2002 |
| EP | 0149578 A2 | 7/1985 |
| EP | 0400974 A2 | 5/1990 |
| EP | 0399285 A1 | 11/1990 |
| EP | 0412358 A1 | 2/1991 |
| EP | 0524482 A1 | 1/1993 |
| EP | 0657454 A1 | 6/1995 |
| EP | 1054012 A1 | 11/2000 |
| EP | 1338595 A2 | 8/2003 |
| EP | 1514552 A1 | 3/2005 |
| EP | 1537880 A1 | 8/2005 |
| ES | 385302 A1 | 4/1973 |
| FR | 2707641 A1 | 1/1995 |
| JP | S37-4895 | 6/1962 |
| JP | 2003/300977 | 10/2003 |
| JP | 2006/045156 | 2/2006 |
| WO | 91/07945 A1 | 6/1991 |
| WO | 94/03456 A1 | 2/1994 |
| WO | 99/29695 A1 | 6/1999 |
| WO | 02/02560 A2 | 1/2002 |
| WO | 02/14271 A1 | 2/2002 |
| WO | 02/24698 A1 | 3/2002 |
| WO | WO 02/068420 A1 | 9/2002 |
| WO | 03/004496 A1 | 1/2003 |
| WO | 03/024965 A2 | 3/2003 |
| WO | 03/057200 A2 | 7/2003 |
| WO | 03/104229 A1 | 12/2003 |
| WO | 2004/018467 A2 | 3/2004 |
| WO | WO 2004/018468 A2 | 3/2004 |
| WO | 2004/028524 A1 | 4/2004 |
| WO | 2004/033455 A2 | 4/2004 |
| WO | 2004/041820 A1 | 5/2004 |
| WO | 2004/046148 A1 | 6/2004 |
| WO | 2004/048379 A1 | 6/2004 |
| WO | 2004/050658 A1 | 6/2004 |
| WO | 2004/096806 A1 | 11/2004 |
| WO | 2004/108730 A1 | 12/2004 |
| WO | 2005/058901 A1 | 6/2005 |
| WO | 2005/082906 A1 | 9/2005 |
| WO | 2005/085246 A1 | 9/2005 |
| WO | 2004/111051 A1 | 12/2005 |
| WO | 2006/029769 A1 | 3/2006 |
| WO | 2006/048427 A1 | 5/2006 |
| WO | 2006/068163 A1 | 6/2006 |
| WO | 2007/017423 A2 | 2/2007 |
| WO | 2008/017670 A1 | 2/2008 |

OTHER PUBLICATIONS

U.S. Appl. No. 11/744,701, filed May 4, 2007, Kohlrausch.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Bollag, R.J. et al; "Osteoblast-Derived Cells Express Functional Glucose-Dependent Insulinotropic Peptide Receptors," Endocrinology, vol. 141, No. 3, 2000, pp. 1228-1235.

Brittain, H.G., "Methods for the Characterization of Polymorphs: X-Ray Powder Diffraction," Polymorphism in Pharmaceutical Solids, 1999, p. 235-238.

Caira, M.R., "Crystalline polymorphism of organic compounds" Topics in Current Chemistry, Springer, Berlin, vol. 198, 1998, p. 163-208.

Conarello, S.L. et al; "Mice lacking dipeptidyl peptidase IV are protected against obesity and insulin resistance," PNAS 2003; 100:6825-6830; originally published online May 14, 2003; information current as of Dec. 2006. www.pnas.org/cgi/content/full/100/11/6825.

Deacon, C.F. et al; "Dipeptidyl peptidase IV inhabitation as an approach to the treatment and prevention of type 2 diabetes: a historical perspective:" Biochemical and Biophysical Research Communications (BBRC) 294 (2002) 1-4.

DeMeester, I. et al.; "CD26, let it cut or cut it down", Review: Immunology Today; Aug. 1999, vol. 20, No. 8 pp. 367-375.

Korom, S. et al; Inhibition of CD26/dipeptidyl peptidase IV activity in vivo prolongs cardiac allograft survival in rat recipients[1,2], Transplantation, May 27, 1997, vol. 63, No. 10, pp. 1495-1500.

Pospisilik, et al; Dipeptidyl Peptidase IV Inhibitor Treatment Stimulates β-Cell Survival and Islet Neogenesis in Streptozotocin-Induced Diabetic Rats; Diabetes, vol. 52, Mar. 2003 pp. 741-750.

Rhee et al.: "Nitrogen-15-Labeled Deoxynucleosides. 3. Synthesis of [3-$^{15}$N]-2'-Deoxyadenosine" J. Am. Chem. Soc. 1990, 112, 8174-8175.

Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.

Tanaka, S.. et al; "Suppression of Arthritis by the Inhibitors of Dipeptidyl Peptidase IV," In. J. Immunopharmac., vol. 19, No. 1, pp. 15-24, 1997.

Wolff, M.E.: "Burger's Medicinal Chemistry and Drug Discovery" Fifth Edition, vol. 1: Principles and Practice, pp. 975-977, 1994, John Wiley & Sons, Inc.

Zhong, Qing et al; "Glucose-dependent insulinotropic peptide stimulates proliferation and TGF-β release from MG-63 cells," Peptides 24 (2003) 611-616.

Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Farmatsevtichnii Zhurnal, 1986, (Kiev), vol. 5, 1986, pp. 41-44.

Chemical Abstracts Accession No. 106:95577 Romanenko et al., "Synthesis and biological activity of 3-methyl, 7-or 8-alkyl-7,8-dialkyl, heterocyclic, and cyclohexylaminoxanthines," Zaporozh. Med. Institute (1986).

Yoshikawa, Seiji et al.: Chemical Abstract of Japanese Patent No. WO 2003/104229 Preparation of purinone derivatives as dipeptidylpeptidase IV (DPP-IV) inhibitors, 2003.

Patani George A. et al.: "Bioisoterism : A Rational Approach in Drug Design", Chemical Reviews, 1996, vol. 96, No. 8, pp. 3147-3176.

International Search Report for PCT/EP03/09127 mailed Nov. 28, 2003.

International Search Report for PCT/EP03/12821 mailed Mar. 30, 2004.

International Search Report for PCT/EP03/13648 mailed Apr. 5, 2004.

International Search Report for PCT/EP2007/054270 mailed Aug. 14, 2007.

International Search Report for PCT/EP2007/058181 mailed Nov. 28, 2007.

International Search Report for PCT/EP2007/054204 mailed Aug. 3, 2007.

International Search Report for PCT/EP2007/054201 mailed Aug. 29, 2007.

Busso et al., "Circulating CD26 is Negatively Associated with Inflammation in Human and Experimental Arthritis," Am. J. Path., vol. 166, No. 2, Feb. 2005, pp. 433-442.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Januvia; Patient Information; Oct. 2007.

Zejc, Alfred et al; Badania Nad Piperazynowymi Pochodnymi Dwumetyloksantyn; Acta Polon. Pharm. XXXV. Nr 4, 1976, pp. 417-421.

* cited by examiner

8-[3-AMINO-PIPERIDIN-1-YL]-XANTHINES, THEIR PREPARATION AND THEIR USE AS PHARMACEUTICAL COMPOSITION

RELATED APPLICATIONS

This application claims the benefit under 35 USC 119(a) of German Patent Application No. 10 2004 009 039, filed Feb. 23, 2004. This application also claims the benefit under 35 USC 119(e) of U.S. Provisional Patent Application No. 60/551,752, filed on Mar. 10, 2004.

DETAILED DESCRIPTION OF THE INVENTION

The present invention relates to new substituted xanthines of general formula

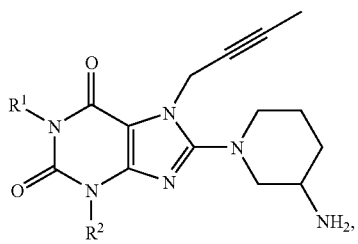

the tautomers, enantiomers, diastereomers, the mixtures thereof, and the salts thereof, particularly the physiologically acceptable salts thereof with inorganic or organic acids or bases that have valuable pharmacological properties, particularly an inhibiting effect on the activity of the enzyme dipeptidylpeptidase-IV (DPP-IV), the preparation thereof, the use thereof for preventing or treating illnesses or conditions connected with an increased DPP-IV activity or capable of being prevented or alleviated by reducing the DPP-IV activity, particularly type I or type II diabetes mellitus, the pharmaceutical compositions containing a compound of general formula (I) or a physiologically acceptable salt thereof, and processes for the preparation thereof.

Structurally similar compounds are described for example in WO 02/068420.

In the above formula I $R^1$ denotes a benzyl, 2-fluorobenzyl, 3-fluorobenzyl, 4-fluorobenzyl, 2-chlorobenzyl, 3-chlorobenzyl, 4-chlorobenzyl, 2-(trifluoromethyl)-benzyl, 3-(trifluoromethyl)-benzyl, or 4-(trifluoromethyl)-benzyl group, a 2-methoxybenzyl, 3-methoxybenzyl, 4-methoxybenzyl, 2-(difluoromethoxy)-benzyl, 3-(difluoromethoxy)-benzyl, 4-(difluoromethoxy)-benzyl, 2-(trifluoromethoxy)-benzyl, 3-(trifluoromethoxy)-benzyl, or 4-(trifluoromethoxy)-benzyl group, a 2-cyanobenzyl, 3-cyanobenzyl, or 4-cyanobenzyl group, a 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, or 2-cyano-6-fluoro-benzyl group, a 2-oxo-2-phenyl-ethyl or 2-(3-methoxy-phenyl)-2-oxo-ethyl group, a 2-(3-methyl-2-oxo-2,3-dihydro-benzoxazol-4-yl)-2-oxo-ethyl group, a (pyridin-2-yl)methyl, (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, or (6-cyano-pyridin-3-yl)methyl group, a (3-cyano-quinolin-2-yl)methyl group, a (1-cyano-isoquinolin-3-yl)methyl or (4-cyano-isoquinolin-1-yl)methyl group, a (4-methyl-quinazolin-2-yl)methyl group, a (quinoxalin-6-yl)methyl or (2,3-dimethyl-quinoxalin-6-yl)methyl group, or a ([1,5]naphthyridin-2-yl)methyl group; and $R^2$ denotes a cyclopropyl or phenyl group, the tautomers, enantiomers, diastereomers, the mixtures thereof, and the salts thereof.

In a second aspect, the invention relates to compounds of general formula (I), wherein $R^1$ is as hereinbefore defined and $R^2$ denotes a cyclopropyl group, the tautomers, enantiomers, diastereomers, the mixtures thereof, and the salts thereof. In a third aspect, the invention relates to compounds of general formula (I), wherein $R^1$ is as hereinbefore defined and $R^2$ denotes a phenyl group, the tautomers, enantiomers, diastereomers, the mixtures thereof and the salts thereof.

According to the invention the compounds of general formula I are obtained by methods known, per se, for example, by the following methods:

a) Reacting a Compound of General Formula

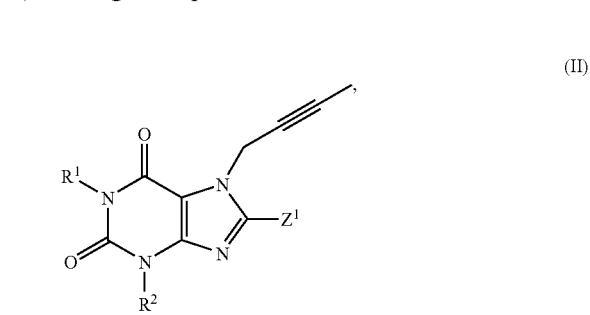

wherein $R^1$ and $R^2$ are as hereinbefore defined; and $Z^1$ denotes a leaving group, such as a halogen atom, a substituted hydroxy, mercapto, sulphinyl, sulphonyl or sulphonyloxy group such as a chlorine or bromine atom, a methanesulphonyl, or methanesulphonyloxy group, with 3-aminopiperidine, the enantiomers thereof, or the salts thereof.

The reaction is expediently carried out in a solvent, such as isopropanol, butanol, tetrahydrofuran, dioxane, dimethylformamide, dimethylsulfoxide, ethyleneglycol monomethylether, ethyleneglycol diethylether, or sulfolane, optionally in the presence of an inorganic or tertiary organic base, e.g., sodium carbonate, potassium carbonate, or potassium hydroxide, a tertiary organic base, e.g., triethylamine, or in the presence of N-ethyl-diisopropylamine (Hünig base), while these organic bases may simultaneously also serve as solvent, and optionally in the presence of a reaction accelerator, such as an alkali metal halide or a palladium-based catalyst at temperatures between −20° C. and 180° C., but preferably at temperatures between −10° C. and 120° C. The reaction may, however, also be carried out without solvent or in an excess of the 3-aminopiperidine.

b) Deprotecting a Compound of General Formula

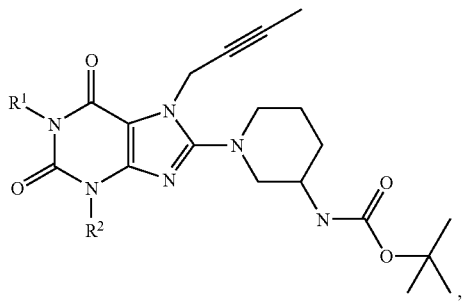

(III)

R¹ and R² are as hereinbefore defined.

The tert.-butyloxycarbonyl group is preferably cleaved by treating with an acid, such as trifluoroacetic acid or hydrochloric acid or by treating with bromotrimethylsilane or iodotrimethylsilane, optionally using a solvent, such as methylene chloride, ethyl acetate, dioxane, methanol, isopropanol, or diethyl ether at temperatures between 0° C. and 80° C.

In the reactions described hereinbefore, any reactive groups present, such as amino, alkylamino, or imino groups, may be protected during the reaction by conventional protecting groups that are cleaved again after the reaction.

For example, a protecting group for an amino, alkylamino, or imino group may be a formyl, acetyl, trifluoroacetyl, ethoxycarbonyl, tert-butoxycarbonyl, benzyloxycarbonyl, benzyl, methoxybenzyl, or 2,4-dimethoxybenzyl group, and additionally, for the amino group, a phthalyl group.

Any protecting group used is optionally, subsequently cleaved, for example, by hydrolysis in an aqueous solvent, e.g., in water, isopropanol/water, acetic acid/water, tetrahydrofuran/water, or dioxane/water, in the presence of an acid, such as trifluoroacetic acid, hydrochloric acid, or sulfuric acid, or in the presence of an alkali metal base, such as sodium hydroxide or potassium hydroxide, or aprotically, e.g., in the presence of iodotrimethylsilane, at temperatures between 0° C. and 120° C., preferably at temperatures between 10° C. and 100° C.

However, a benzyl, methoxybenzyl, or benzyloxycarbonyl group is cleaved, for example, hydrogenolytically, e.g., with hydrogen in the presence of a catalyst, such as palladium/charcoal, in a suitable solvent, such as methanol, ethanol, ethyl acetate, or glacial acetic acid, optionally with the addition of an acid, such as hydrochloric acid, at temperatures between 0° C. and 100° C., but preferably at ambient temperatures between 20° C. and 60° C., and at a hydrogen pressure of 1 to 7 bar, but preferably from 3 to 5 bar. However, a 2,4-dimethoxybenzyl group is preferably cleaved in trifluoroacetic acid in the presence of anisole.

A tert.-butyloxycarbonyl group is preferably cleaved by treating with an acid, such as trifluoroacetic acid or hydrochloric acid, or by treating with iodotrimethylsilane, optionally using a solvent, such as methylene chloride, dioxane, methanol, or diethyl ether.

A trifluoroacetyl group is preferably cleaved by treating with an acid, such as hydrochloric acid, optionally in the presence of a solvent, such as acetic acid, at temperatures between 50° C. and 120° C., or by treating with sodium hydroxide solution, optionally in the presence of a solvent, such as tetrahydrofuran, at temperatures between 0° C. and 50° C.

A phthalyl group is preferably cleaved in the presence of hydrazine or a primary amine, such as methylamine, ethylamine, ethanolamine, or n-butylamine, in a solvent, such as methanol, ethanol, isopropanol, toluene/water, or dioxane, at temperatures between 20° C. and 50° C.

Moreover, the compounds of general formula I obtained may be resolved into their enantiomers and/or diastereomers, as mentioned hereinbefore. Thus, for example, cis/trans mixtures may be resolved into their cis and trans isomers, and compounds with at least one optically active carbon atom may be separated into their enantiomers.

Thus, for example, the cis/trans mixtures obtained may be separated by chromatography into their cis and trans isomers, the compounds of general formula I obtained that occur as racemates may be separated by methods known, per se, (cf. Allinger N. L. and Eliel E. L. in "Topics in Stereochemistry", Vol. 6, Wiley Interscience, 1971), into their optical enantiomers, and compounds of general formula I with at least two asymmetric carbon atoms may be resolved into their diastereomers on the basis of their physical-chemical differences using methods known, per se, e.g., by chromatography and/or fractional crystallisation, and, if these compounds are obtained in racemic form, they may subsequently be resolved into the enantiomers as mentioned above.

The enantiomers are preferably separated by column separation on chiral phases, or by recrystallisation from an optically active solvent, or by reacting with an optically active substance that forms salts or derivatives, such as, e.g., esters or amides with the racemic compound, particularly acids, and the activated derivatives or alcohols thereof, and separating the diastereomeric mixture of salts or derivatives thus obtained, e.g., on the basis of their differences in solubility, whereas the free antipodes may be released from the pure diastereomeric salts or derivatives by the action of suitable agents. Optically active acids in common use are, e.g., the D- and L-forms of tartaric acid, or dibenzoyltartaric acid, di-o-tolyltartaric acid, malic acid, mandelic acid, camphorsulfonic acid, glutamic acid, aspartic acid, or quinic acid. An optically active alcohol may be, for example, (+) or (−)-menthol and an optically active acyl group in amides, for example, may be a (+)- or (−)-menthyloxycarbonyl.

Furthermore, the compounds of formula I obtained may be converted into the salts thereof, particularly, for pharmaceutical use, into the physiologically acceptable salts, with inorganic or organic acids. Acids that may be used for this purpose include, for example, hydrochloric acid, hydrobromic acid, sulfuric acid, methanesulfonic acid, phosphoric acid, fumaric acid, succinic acid, lactic acid, citric acid, tartaric acid, or maleic acid.

The compounds of general formulae II and III used as starting compounds are either known from the literature or may be prepared by methods known from the literature (see Examples I to VII).

As already mentioned hereinbefore, the compounds of general formula I according to the invention and the physiologically acceptable salts thereof have valuable pharmacological properties, particularly an inhibiting effect on the enzyme DPP-IV.

The biological properties of the new compounds were investigated as follows:

The ability of the substances and their corresponding salts to inhibit the DPP-IV activity can be demonstrated in an experiment in which an extract of the human colon carcinoma cell line Caco-2 is used as the DPP IV source. The differentiation of the cells in order to induce the DPP-IV expression was carried out in accordance with the description by Reiher et al. in an article entitled "Increased expression of intestinal cell line Caco-2" that appeared in Proc. Natl. Acad. Sci. Vol. 90, pp. 5757-5761 (1993). The cell extract was obtained from cells solubilized in a buffer (10 mM Tris HCl, 0.15 M NaCl, 0.04 t.i.u. aprotinin, 0.5% Nonidet-P40, pH 8.0) by centrifugation at 35,000 g for 30 minutes at 4° C. (to remove cell debris).

The DPP-IV assay was carried out as follows:

50 µl of substrate solution (AFC; AFC is amido-4-trifluoromethylcoumarin), final concentration 100 µM, was placed in black microtitre plates. 20 µl of assay buffer (final concentrations 50 mM Tris HCl pH 7.8, 50 mM NaCl, 1% DMSO) was pipetted therein. The reaction was started by the addition of 30 µl of solubilized Caco-2 protein (final concentration 0.14 µg of protein per well). The test substances under investigation were typically added prediluted to 20 µl, while the volume of assay buffer was then reduced accordingly. The reaction was carried out at ambient temperature, the incubation period was 60 minutes. Then the fluorescence was measured in a Victor 1420 Multilabel Counter, with the excitation wavelength at 405 nm and the emission wavelength at 535 nm. Dummy values (corresponding to 0% activity) were obtained in mixtures with no Caco-2 protein (volume replaced by assay buffer), control values (corresponding to 100% activity) were obtained in mixtures without any added substance. The potency of the test substances in question, expressed as $IC_{50}$ values, were calculated from dosage/activity curves consisting of 11 measured points in each case. The following results were obtained:

| Compound (Example no.) | DPP IV inhibition $IC_{50}$ [nM] |
|---|---|
| 1-[2-(3-methyl-2-oxo-2,3-dihydro-benzoxazol-4-yl)-2-oxo-ethyl]-3-cyclopropyl-7-(2-butyn-1-yl)-8-[(R)-3-(tert.-butyloxycarbonylamino)-piperidin-1-yl]-xanthine (Example No. 1) | 3.6 |
| 1-[(4-methyl-quinazolin-2-yl)methyl]-3-cyclopropyl-7-(2-butyn-1-yl)-8-[(R)-3-(tert.-butyloxycarbonylamino)-piperidin-1-yl]-xanthine (Example No. 1(1)) | 2.7 |
| 1-[(4-methyl-quinazolin-2-yl)methyl]-3-phenyl-7-(2-butyn-1-yl)-8-[(R)-3-(tert.-butyloxycarbonylamino)-piperidin-1-yl]-xanthine (Example 1(8)) | 4.9 |
| 1-[2-(3-methoxy-phenyl)-2-oxo-ethyl]-3-phenyl-7-(2-butyn-1-yl)-8-[(R)-3-(tert.-butyloxycarbonylamino)-piperidin-1-yl]-xanthine (Example No. 1(10)) | 8.1 |
| 1-[([1,5]naphthyridin-2-yl)methyl]-3-phenyl-7-(2-butyn-1-yl)-8-[(R)-3-(tert.-butyloxycarbonylamino)-piperidin-1-yl]-xanthine (Example No. 1(13)) | 4.0 |
| 1-(2-cyano-benzyl)-3-phenyl-7-(2-butyn-1-yl)-8-[(R)-3-(tert.-butyloxycarbonylamino)-piperidin-1-yl]-xanthine (Example No. 1(15)) | 1.5 |

The compounds prepared according to the invention are well tolerated, as no toxic side effects could be detected in rats after the oral administration of 10 mg/kg of the compound of Example 1(8), for example.

In view of their ability to inhibit DPP-IV activity, the compounds of general formula I according to the invention and the corresponding pharmaceutically acceptable salts thereof are suitable for influencing any conditions or diseases which can be affected by the inhibition of the DPP-IV activity. It is therefore to be expected that the compounds according to the invention will be suitable for the prevention or treatment of diseases or conditions such as type I and type II diabetes mellitus, pre-diabetes, reduced glucose tolerance or changes in the fasting blood sugar, diabetic complications (e.g., retinopathy, nephropathy, or neuropathies), metabolic acidosis or ketosis, reactive hypoglycemia, insulin resistance, metabolic syndrome, dyslipidemias of various origins, arthritis, atherosclerosis and related diseases, obesity, allograft transplantation, and osteoporosis caused by calcitonin. In addition, these substances are suitable for preventing B-cell degeneration, such as, e.g., apoptosis or necrosis of pancreatic B-cells. The substances are also suitable for improving or restoring the function of pancreatic cells and additionally increasing the size and number of pancreatic B-cells. Additionally, on the basis of the role of the glucagon-like peptides, such as, e.g., GLP-1 and GLP-2 and their link with DPP-IV inhibition, it is expected that the compounds according to the invention will be suitable for achieving, inter alia, a sedative or tranquillising effect, as well as having a favorable effect on catabolic states after operations or hormonal stress responses or possibly reducing mortality and morbidity after myocardial infarct. Moreover, they are suitable for treating any conditions connected with the effects mentioned above and mediated by GLP-1 or GLP-2. The compounds according to the invention may also be used as diuretics or antihypertensives and are suitable for preventing and treating acute kidney failure. The compounds according to the invention may also be used to treat inflammatory complaints of the respiratory tract. They are also suitable for preventing and treating chronic inflammatory bowel diseases, such as, e.g., irritable bowel syndrome (IBS), Crohn's disease, or ulcerative colitis, and also pancreatitis. It is also expected that they can be used for all kinds of injury or damage to the gastrointestinal tract such as may occur in colitis and enteritis, for example. Moreover, it is expected that DPP-IV inhibitors and hence the compounds according to the invention can be used to treat infertility or to improve fertility in humans or mammals, particularly if the infertility is connected with insulin resistance or with polycystic ovary syndrome. On the other hand, these substances are suitable for influencing sperm motility and are thus suitable for use as male contraceptives. In addition, the substances are suitable for treating growth hormone deficiencies connected with restricted growth, and may reasonably be used for all indications for which growth hormone may be used. The compounds according to the invention are also suitable, on the basis of their inhibitory effect on DPP-IV, for treating various autoimmune diseases such as, e.g., rheumatoid arthritis, multiple sclerosis, thyroiditis, and Basedow's disease, etc. They may also be used to treat viral diseases and also, for example, in HIV infections, for stimulating blood production, in benign prostatic hyperplasia, gingivitis, as well as for the treatment of neuronal defects and neurodegenerative diseases, such as Alzheimer's disease, for example. The compounds described may also be used for the treatment of tumors, particularly for modifying tumor invasion and also metastasisation; examples here are their use in treating T-cell lymphomas, acute lymphoblastic leukemia, cell-based pancreatic carcinomas, basal cell carcinomas, or breast cancers. Other indications are stroke, ischemia of various origins, Parkinson's disease, and migraine. In addition, further indications include follicular and epidermal hyperkeratoses, increased keratinocyte proliferation, psoriasis, encephalomyelitis, glomerulonephritis, lipodystrophies, as well as psychosomatic, depressive, and neuropsychiatric diseases of all kinds.

The compounds according to the invention may also be used in conjunction with other active substances. Suitable therapeutic agents for such combinations include, for example, antidiabetic agents, such as metformin, sulfonylureas (e.g., glibenclamid, tolbutamide, glimepiride), nateglinide, repaglinide, thiazolidinediones (e.g., rosiglitazone, pioglitazone), PPAR-gamma agonists (e.g., GI 262570) and antagonists, PPAR-gamma/alpha modulators (e.g., KRP 297), PPAR-gamma/alpha/delta modulators, AMPK activators, ACC1 and ACC2 inhibitors, DGAT inhibitors, SMT3 receptor agonists, 11β-HSD inhibitors, FGF19 agonists or mimetics, alpha-glucosidase inhibitors (e.g., acarbose, voglibose), other DPP-IV inhibitors, alpha2 antagonists, insulin and insulin analogues, GLP-1 and GLP-1 analogues (e.g., exendin-4), or amylin. Also, combinations with SGLT2 inhibitors, such as T-1095 or KGT-1251 (869682), inhibitors of protein tyrosine phosphatase 1, substances which influence deregulated glucose production in the liver, such as, e.g., inhibitors of glucose-6-phosphatase, or fructose-1,6-bisphosphatase, glycogen phosphorylase, glucagon receptor antagonists and inhibitors of phosphoenol-pyruvate carboxykinase, glycogen synthase kinase or pyruvate dehydrokinase, lipid lowering agents, such as HMG-CoA-reductase inhibitors (e.g., simvastatin, atorvastatin), fibrates (e.g., bezafibrate, fenofibrate), nicotinic acid and its derivatives, PPAR-alpha agonists, PPAR-delta agonists, ACAT inhibitors (e.g., avasimibe), or cholesterol absorption inhibitors, such as, for example, ezetimibe, bile acid-binding substances, such as, for example, cholestyramine, inhibitors of ileac bile acid transport, HDL-raising compounds, such as, for example, inhibitors of CETP, or regulators of ABC1 or LXRalpha antagonists, LXRbeta agonists or LXRalpha/beta regulators, or active substances for the treatment of obesity, such as e.g., sibutramine or tetrahydrolipostatin, dexfenfluramine, axokine, antagonists of the cannabinoid1 receptor, MCH-1 receptor antagonists, MC4 receptor agonists, NPY5 or NPY2 antagonists, or $β_3$-agonists, such as SB-418790 or AD-9677, as well as agonists of the 5HT2c receptor.

It is also possible to combine the compounds with drugs for treating high blood pressure, such as, e.g., all antagonists or ACE inhibitors, diuretics, β-blockers, Ca-antagonists, etc., or combinations thereof.

The dosage required to achieve such an effect is expediently, by intravenous route, 1 to 100 mg, preferably 1 to 30 mg, and by oral route 1 to 1000 mg, preferably 1 to 100 mg, in each case 1 to 4 times a day. For this purpose, the compounds of formula I prepared according to the invention, optionally combined with other active substances, may be incorporated together with one or more inert conventional carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose, or fatty substances, such as hard fat or suitable mixtures thereof, into conventional galenic preparations, such as plain or coated tablets, capsules, powders, suspensions, or suppositories.

The Examples that follow are intended to illustrate the invention:

Preparation of the Starting Compounds

EXAMPLE I

1-[2-(3-methyl-2-oxo-2,3-dihydro-benzoxazol-4-yl)-2-oxo-ethyl]-3-cyclopropyl-7-(2-butyn-1-yl)-8-[(R)-3-(tert.-butyloxycarbonylamino)-piperidin-1-yl]-xanthine A mixture of 250 mg of 3-cyclopropyl-7-(2-butyn-1-yl)-8-[(R)-3-(tert.-butyloxycarbonylamino)-piperidin-1-yl]-xanthine, 175 mg of 4-(2-bromo-acetyl)-3-methyl-3H-benzoxazol-2-one and 300 mg potassium carbonate in 3 ml N,N-dimethylformamide is stirred for one hour at 75° C., then another 60 mg of 4-(2-bromo-acetyl)-3-methyl-3H-benzoxazol-2-one are added. After a further 1.5 hours the reaction is complete and the reaction mixture is combined with ice water. The precipitate that crystallises out is suction filtered, washed with water and dissolved in methylene chloride. The solution is dried over magnesium sulphate and evaporated down. The crude product is brought to crystallisation with diethyl ether, suction filtered and dried.

Yield: 310 mg (87% of theory)

$R_f$ value: 0.56 (silica gel, methylene chloride/methanol=95:5)

Mass spectrum (ESI$^+$): m/z=632 [M+H]$^+$

The following compounds are obtained analogously to Example I:

(1) 1-[(4-methyl-quinazolin-2-yl)methyl]-3-cyclopropyl-7-(2-butyn-1-yl)-8-[(R)-3-(tert.-butyloxycarbonylamino)-piperidin-1-yl]-xanthine $R_f$ value: 0.40 (silica gel, ethyl acetate)

Mass spectrum (ESI$^+$): m/z=599 [M+H]$^+$ (2) 1-[2-(3-methoxy-phenyl)-2-oxo-ethyl]-3-cyclopropyl-7-(2-butyn-1-yl)-8-[(R)-3-(tert.-butyloxycarbonylamino)-piperidin-1-yl]-xanthine $R_f$ value: 0.60 (silica gel, methylene chloride/ethyl acetate=1:1)

Mass spectrum (ESI$^+$): m/z=591 [M+H]$^+$ (3) 1-[(4-cyano-isoquinolin-1-yl)methyl]-3-cyclopropyl-7-(2-butyn-1-yl)-8-[(R)-3-(tert.-butyloxycarbonylamino)-piperidin-1-yl]-xanthine $R_f$ value: 0.65 (silica gel, ethyl acetate)

Mass spectrum (ESI$^+$): m/z=609 [M+H]$^+$ (4) 1-[(1-cyano-isoquinolin-3-yl)methyl]-3-cyclopropyl-7-(2-butyn-1-yl)-8-[(R)-3-(tert.-butyloxycarbonylamino)-piperidin-1-yl]-xanthine $R_f$ value: 0.59 (silica gel, ethyl acetate/petroleum ether=4:1)

Mass spectrum (ESI$^+$): m/z=609 [M+H]$^+$ (5) 1-[([1,5]naphthyridin-2-yl)methyl]-3-cyclopropyl-7-(2-butyn-1-yl)-8-[(R)-3-(tert.-butyloxycarbonylamino)-piperidin-1-yl]-xanthine $R_f$ value: 0.48 (silica gel, ethyl acetate/methanol=95:5)

Mass spectrum (ESI$^+$): m/z=585 [M+H]$^+$ (6) 1-[(2,3-dimethyl-quinoxalin-6-yl)methyl]-3-cyclopropyl-7-(2-butyn-1-yl)-8-[(R)-3-(tert.-butyloxycarbonylamino)-piperidin-1-yl]-xanthine $R_f$ value: 0.38 (silica gel, ethyl acetate)

Mass spectrum (ESI$^+$): m/z=613 [M+H]$^+$ (7) 1-(2-oxo-2-phenyl-ethyl)-3-phenyl-7-(2-butyn-1-yl)-8-[(R)-3-(tert.-butyloxycarbonylamino)-piperidin-1-yl]-xanthine $R_f$ value: 0.65 (silica gel, methylene chloride/ethyl acetate=7:3)

Mass spectrum (ESI$^+$): m/z=597 [M+H]$^+$ (8) 1-[(4-methyl-quinazolin-2-yl)methyl]-3-phenyl-7-(2-butyn-1-yl)-8-[(R)-3-(tert.-butyloxycarbonylamino)-piperidin-1-yl]-xanthine $R_f$ value: 0.67 (silica gel, methylene chloride/methanol/conc. aqueous ammonia=90:10:1)

Mass spectrum (ESI$^+$): m/z=635 [M+H]$^+$ (9) 1-[2-(3-methyl-2-oxo-2,3-dihydro-benzoxazol-4-yl)-2-oxo-ethyl]-3-phenyl-7-(2-butyn-1-yl)-8-[(R)-3-(tert.-butyloxycarbonylamino)-piperidin-1-yl]-xanthine $R_f$ value: 0.52 (silica gel, methylene chloride/methanol=95:5)

Mass spectrum (ESI⁺): m/z=668 [M+H]⁺

(10) 1-[2-(3-methoxy-phenyl)-2-oxo-ethyl]-3-phenyl-7-(2-butyn-1-yl)-8-[(R)-3-(tert.-butyloxycarbonylamino)-piperidin-1-yl]-xanthine $R_f$ value: 0.85 (silica gel, methylene chloride/ethyl acetate=1:1)

Mass spectrum (ESI⁺): m/z=627 [M+H]⁺

(11) 1-[(4-cyano-isoquinolin-1-yl)methyl]-3-phenyl-7-(2-butyn-1-yl)-8-[(R)-3-(tert.-butyloxycarbonylamino)-piperidin-1-yl]-xanthine $R_f$ value: 0.85 (silica gel, ethyl acetate)

Mass spectrum (ESI⁺): m/z=645 [M+H]⁺

(12) 1-[(1-cyano-isoquinolin-3-yl)methyl]-3-phenyl-7-(2-butyn-1-yl)-8-[(R)-3-(tert.-butyloxycarbonylamino)-piperidin-1-yl]-xanthine $R_f$ value: 0.74 (silica gel, ethyl acetate/petroleum ether=4:1)

Mass spectrum (ESI⁺): m/z=645 [M+H]⁺

(13) 1-[([1,5]naphthyridin-2-yl)methyl]-3-phenyl-7-(2-butyn-1-yl)-8-[(R)-3-(tert.-butyloxycarbonylamino)-piperidin-1-yl]-xanthine $R_f$ value: 0.62 (silica gel, ethyl acetate/methanol=95:5)

Mass spectrum (ESI⁺): m/z=621 [M+H]⁺

(14) 1-[(2,3-dimethyl-quinoxalin-6-yl)methyl]-3-phenyl-7-(2-butyn-1-yl)-8-[(R)-3-(tert.-butyloxycarbonylamino)-piperidin-1-yl]-xanthine $R_f$ value: 0.59 (silica gel, ethyl acetate)

Mass spectrum (ESI⁺): m/z=649 [M+H]⁺

(15) 1-(2-cyano-benzyl)-3-phenyl-7-(2-butyn-1-yl)-8-[(R)-3-(tert.-butyloxycarbonylamino)-piperidin-1-yl]-xanthine $R_f$ value: 0.90 (silica gel, methylene chloride/ethyl acetate=1:1)

Mass spectrum (ESI⁺): m/z=594 [M+H]⁺

(17) 1-(2-cyano-benzyl)-3-cyclopropyl-7-(2-butyn-1-yl)-8-[(R)-3-(tert.-butyloxy-carbonylamino)-piperidin-1-yl]-xanthine $R_f$ value: 0.70 (silica gel, methylene chloride/ethyl acetate=1:1)

Mass spectrum (ESI⁺): m/z=558 [M+H]⁺

EXAMPLE II

3-Cyclopropyl-7-(2-butyn-1-yl)-8-[(R)-3-(tert.-butyloxycarbonylamino)-piperidin-1-yl]-xanthine Prepared by reacting 3-cyclopropyl-7-(2-butyn-1-yl)-8-bromo-xanthine with (R)-3-tert.-butyloxycarbonylamino-piperidine in the presence of potassium carbonate in dimethylsulphoxide at 80° C.

$R_f$ value: 0.35 (reversed phase ready-made TLC plate (E. Merck), acetonitrile/water/trifluoroacetic acid=50:50:1)

Mass spectrum (ESI⁺): m/z=443 [M+H]⁺

The following compound is obtained analogously to Example II:

(1) 3-phenyl-7-(2-butyn-1-yl)-8-[(R)-3-(tert.-butyloxycarbonylamino)-piperidin-1-yl]-xanthine $R_f$ value: 0.25 (reversed phase ready-made TLC plate (E. Merck), acetonitrile/water/trifluoroacetic acid=50:50:1)

Mass spectrum (ESI⁺): m/z=479 [M+H]⁺

EXAMPLE III

3-Cyclopropyl-7-(2-butyn-1-yl)-8-bromo-xanthine

Prepared by reacting 3-cyclopropyl-8-bromo-xanthine with 1-bromo-2-butyne in the presence of diisopropylethylamine in N,N-dimethylformamide at ambient temperature.

$R_f$ value: 0.45 (reversed phase ready-made TLC plate (E. Merck), acetonitrile/water/trifluoroacetic acid=50:50:1)

Mass spectrum (ESI⁺): m/z=323, 325 [M+H]⁺

The following compound is obtained analogously to Example III:

(1) 3-phenyl-7-(2-butyn-1-yl)-8-bromo-xanthine $R_f$ value: 0.41 (reversed phase ready-made TLC plate (E. Merck), acetonitrile/water/trifluoroacetic acid=50:50:1)

Mass spectrum (ESI⁺): m/z=359, 361 [M+H]⁺

EXAMPLE IV

3-Cyclopropyl-8-bromo-xanthine

Prepared by reacting 3-cyclopropyl-xanthine with bromine in the presence of potassium carbonate in acetonitrile at 60° C.

$R_f$ value: 0.65 (reversed phase ready-made TLC plate (E. Merck), acetonitrile/water/trifluoroacetic acid=50:50:1)

Mass spectrum (ESI⁺): m/z=271, 273 [M+H]⁺

The following compound is obtained analogously to Example IV:

(1) 3-phenyl-8-bromo-xanthine $R_f$ value: 0.54 (reversed phase ready-made TLC plate (E. Merck), acetonitrile/water/trifluoroacetic acid=50:50:1)

Mass spectrum (ESI⁺): m/z=307, 309 [M+H]⁺

EXAMPLE V 4-(2-Bromo-acetyl)-3-methyl-3H-benzoxazol-2-one

Prepared by bromination of 4-acetyl-3-methyl-3H-benzoxazol-2-on in methylene chloride at ambient temperature.

$R_f$ value: 0.50 (silica gel, petroleum ether/ethyl acetate=2:1)

Mass spectrum (ESI⁺): m/z=270, 272 [M+H]⁺

EXAMPLE VI

4-Acetyl-3-methyl-3H-benzoxazol-2-one

Prepared by reacting 4-acetyl-3H-benzoxazol-2-one with methyl iodide in the presence of potassium-tert.-butoxide in N,N-dimethylformamide at ambient temperature.

$R_f$ value: 0.40 (silica gel, petroleum ether/ethyl acetate=2:1)

Mass spectrum (ESI⁺): m/z=192 [M+H]⁺

EXAMPLE VII

1-Bromomethyl-4-cyano-isoquinoline

Prepared by treating 1-methyl-4-cyano-isoquinoline with N-bromo-succinimide in the presence of azobisisobutyronitrile in carbon tetrachloride at reflux temperature.

$R_f$ value: 0.58 (silica gel, methylene chloride)

Mass spectrum (ESI⁺): m/z=247, 249 [M+H]⁺

The following compounds are obtained analogously to Example VII:

(1) 3-bromomethyl-1-cyano-isoquinoline $R_f$ value: 0.61 (silica gel, methylene chloride)

Mass spectrum (ESI⁺): m/z=247, 249 [M+H]⁺

(2) 2-bromomethyl-[1,5]naphthyridine
$R_f$ value: 0.60 (aluminium oxide, methylene chloride)
Mass spectrum (ESI$^+$): m/z=223, 225 [M+H]$^+$ Preparation of the End Compounds

EXAMPLE 1

1-[2-(3-Methyl-2-oxo-2,3-dihydro-benzoxazol-4-yl)-2-oxo-ethyl]-3-cyclopropyl-7-(2-butyn-1-yl)-8-((R)-3-amino-piperidin-1-yl)-xanthine 1.5 ml isopropanolic hydrochloric acid (5-6 M) are added to 300 mg 1-[2-(3-methyl-2-oxo-2,3-dihydro-benzoxazol-4-yl)-2-oxo-ethyl]-3-cyclopropyl-7-(2-butyn-1-yl)-8-[(R)-3-(tert.-butyloxycarbonylamino)-piperidin-1-yl]-xanthine in 5 ml methylene chloride and the reaction mixture is stirred for 5.5 hours at ambient temperature.

Then the mixture is made alkaline with 8 ml 1N sodium hydroxide solution and extracted with a mixture of methylene chloride and methanol. The combined organic phases are washed with saturated sodium chloride solution, dried over magnesium sulphate and evaporated down. The flask residue is chromatographed through a silica gel column with methylene chloride/methanol/methanolic ammonia solution (98:2:0 to 94:5:1) as eluant. The crude product is brought to crystallisation with diethyl ether, suction filtered, washed and dried.

Yield: 140 mg (55% of theory)
melting point: 168-171° C.
Mass spectrum (ESI$^+$): m/z=532 [M+H]$^+$ The following compounds are obtained analogously to Example 1:

(1) 1-[(4-methyl-quinazolin-2-yl)methyl]-3-cyclopropyl-7-(2-butyn-1-yl)-8-((R)-3-amino-piperidin-1-yl)-xanthine
(BOC cleaving carried out with trifluoroacetic acid)
$R_f$ value: 0.55 (reversed phase ready-made TLC plate (E. Merck), acetonitrile/water/trifluoroacetic acid=50:50:1)
Mass spectrum (ESI$^+$): m/z=499 [M+H]$^+$ (2) 1-[2-(3-methoxy-phenyl)-2-oxo-ethyl]-3-cyclopropyl-7-(2-butyn-1-yl)-8-((R)-3-amino-piperidin-1-yl)-xanthine
(BOC cleaving carried out with trifluoroacetic acid)
$R_f$ value: 0.35 (reversed phase ready-made TLC plate (E. Merck), acetonitrile/water/trifluoroacetic acid=50:50:1)
Mass spectrum (ESI$^+$): m/z=491 [M+H]$^+$ (3) 1-[(4-cyano-isoquinolin-1-yl)methyl]-3-cyclopropyl-7-(2-butyn-1-yl)-8-((R)-3-amino-piperidin-1-yl)-xanthine
$R_f$ value: 0.38 (silica gel, methylene chloride/methanol/conc. aqueous ammonia=90:10:1)
Mass spectrum (ESI$^+$): m/z=509 [M+H]$^+$ (4) 1-[(1-cyano-isoquinolin-3-yl)methyl]-3-cyclopropyl-7-(2-butyn-1-yl)-8-((R)-3-amino-piperidin-1-yl)-xanthine
$R_f$ value: 0.32 (silica gel, methylene chloride/methanol/conc. aqueous ammonia=90:10:1)
Mass spectrum (ESI$^+$): m/z=509 [M+H]$^+$ (5) 1-[([1,5]naphthyridin-2-yl)methyl]-3-cyclopropyl-7-(2-butyn-1-yl)-8-((R)-3-amino-piperidin-1-yl)-xanthine
$R_f$ value: 0.39 (silica gel, methylene chloride/methanol/conc. aqueous ammonia=90:10:1)
Mass spectrum (ESI$^+$): m/z=485 [M+H]$^+$ (6) 1-[(2,3-dimethyl-quinoxalin-6-yl)methyl]-3-cyclopropyl-7-(2-butyn-1-yl)-8-((R)-3-amino-piperidin-1-yl)-xanthine
$R_f$ value: 0.50 (silica gel, methylene chloride/methanol/conc. aqueous ammonia=90:10:1)
Mass spectrum (ESI$^+$): m/z=513 [M+H]$^+$ (7) 1-(2-oxo-2-phenyl-ethyl)-3-phenyl-7-(2-butyn-1-yl)-8-((R)-3-amino-piperidin-1-yl)-xanthine
$R_f$ value: 0.40 (silica gel, methylene chloride/methanol/conc. aqueous ammonia=90:10:1)
Mass spectrum (ESI$^+$): m/z=497 [M+H]$^+$ (8) 1-[(4-methyl-quinazolin-2-yl)methyl]-3-phenyl-7-(2-butyn-1-yl)-8-((R)-3-amino-piperidin-1-yl)-xanthine
$R_f$ value: 0.32 (silica gel, methylene chloride/methanol/conc. aqueous ammonia=90:10:1)
Mass spectrum (ESI$^+$): m/z=535 [M+H]$^+$ (9) 1-[2-(3-methyl-2-oxo-2,3-dihydro-benzoxazol-4-yl)-2-oxo-ethyl]-3-phenyl-7-(2-butyn-1-yl)-8-((R)-3-amino-piperidin-1-yl)-xanthine
$R_f$ value: 0.53 (silica gel, methylene chloride/methanol/conc. aqueous ammonia=90:10:1)
Mass spectrum (ESI$^+$): m/z=568 [M+H]$^+$

(10) 1-[2-(3-methoxy-phenyl)-2-oxo-ethyl]-3-phenyl-7-(2-butyn-1-yl)-8-((R)-3-amino-piperidin-1-yl)-xanthine
$R_f$ value: 0.30 (reversed phase ready-made TLC plate (E. Merck), acetonitrile/water/trifluoroacetic acid=50:50:1)
Mass spectrum (ESI$^+$): m/z=527 [M+H]$^+$

(11) 1-[(4-cyano-isoquinolin-1-yl)methyl]-3-phenyl-7-(2-butyn-1-yl)-8-((R)-3-amino-piperidin-1-yl)-xanthine
$R_f$ value: 0.45 (silica gel, methylene chloride/methanol/conc. aqueous ammonia=90:10:1)
Mass spectrum (ESI$^+$): m/z=545 [M+H]$^+$

(12) 1-[(1-cyano-isoquinolin-3-yl)methyl]-3-phenyl-7-(2-butyn-1-yl)-8-((R)-3-amino-piperidin-1-yl)-xanthine
$R_f$ value: 0.37 (silica gel, methylene chloride/methanol/conc. aqueous ammonia=90:10:1)
Mass spectrum (ESI$^+$): m/z=545 [M+H]$^+$

(13) 1-[([1,5]naphthyridin-2-yl)methyl]-3-phenyl-7-(2-butyn-1-yl)-8-((R)-3-amino-piperidin-1-yl)-xanthine
$R_f$ value: 0.42 (silica gel, methylene chloride/methanol/conc. aqueous ammonia=90:10:1)
Mass spectrum (ESI$^+$): m/z=521 [M+H]$^+$

(14) 1-[(2,3-dimethyl-quinoxalin-6-yl)methyl]-3-phenyl-7-(2-butyn-1-yl)-8-((R)-3-amino-piperidin-1-yl)-xanthine
$R_f$ value: 0.51 (silica gel, methylene chloride/methanol/conc. aqueous ammonia=90:10:1)
Mass spectrum (ESI$^+$): m/z=549 [M+H]$^+$

(15) 1-(2-cyano-benzyl)-3-phenyl-7-(2-butyn-1-yl)-8-((R)-3-amino-piperidin-1-yl)-xanthine
(BOC cleaving carried out with trifluoroacetic acid)
$R_f$ value: 0.45 (reversed phase ready-made TLC plate (E. Merck), acetonitrile/water/trifluoroacetic acid=50:50:1)
Mass spectrum (ESI$^+$): m/z=494 [M+H]$^+$

(16) 1-(2-cyano-benzyl)-3-cyclopropyl-7-(2-butyn-1-yl)-8-((R)-3-amino-piperidin-1-yl)-xanthine
$R_f$ value: 0.45 (reversed phase ready-made TLC plate (E. Merck), acetonitrile/water/trifluoroacetic acid=50:50:1)
Mass spectrum (ESI$^+$): m/z=458 [M+H]$^+$ The following compounds may also be obtained analogously to the foregoing Examples and other methods known from the literature:

(1) 1-(2-cyano-4-fluoro-benzyl)-3-phenyl-7-(2-butyn-1-yl)-8-((R)-3-amino-piperidin-1-yl)-xanthine
(2) 1-(2-cyano-5-fluoro-benzyl)-3-phenyl-7-(2-butyn-1-yl)-8-((R)-3-amino-piperidin-1-yl)-xanthine
(3) 1-(2-cyano-6-fluoro-benzyl)-3-phenyl-7-(2-butyn-1-yl)-8-((R)-3-amino-piperidin-1-yl)-xanthine
(4) 1-(3-cyanobenzyl)-3-phenyl-7-(2-butyn-1-yl)-8-((R)-3-amino-piperidin-1-yl)-xanthine
(5) 1-(4-cyanobenzyl)-3-phenyl-7-(2-butyn-1-yl)-8-((R)-3-amino-piperidin-1-yl)-xanthine
(6) 1-benzyl-3-phenyl-7-(2-butyn-1-yl)-8-((R)-3-amino-piperidin-1-yl)-xanthine (7) 1-[(pyridin-2-yl)methyl]-3-phenyl-7-(2-butyn-1-yl)-8-((R)-3-amino-piperidin-1-yl)-xanthine
(8) 1-(2-chlorobenzyl)-3-phenyl-7-(2-butyn-1-yl)-8-((R)-3-amino-piperidin-1-yl)-xanthine
(9) 1-(2-fluoro-benzyl)-3-phenyl-7-(2-butyn-1-yl)-8-((R)-3-amino-piperidin-1-yl)-xanthine
(10) 1-[(3-cyano-pyridin-2-yl)methyl]-3-phenyl-7-(2-butyn-1-yl)-8-((R)-3-amino-piperidin-1-yl)-xanthine
(11) 1-[(6-cyano-pyridin-2-yl)methyl]-3-phenyl-7-(2-butyn-1-yl)-8-((R)-3-amino-piperidin-1-yl)-xanthine
(12) 1-[(5-cyano-pyridin-2-yl)methyl]-3-phenyl-7-(2-butyn-1-yl)-8-((R)-3-amino-piperidin-1-yl)-xanthine
(13) 1-[(4-cyano-pyridin-2-yl)methyl]-3-phenyl-7-(2-butyn-1-yl)-8-((R)-3-amino-piperidin-1-yl)-xanthine
(14) 1-[(4-cyano-pyridin-3-yl)methyl]-3-phenyl-7-(2-butyn-1-yl)-8-((R)-3-amino-piperidin-1-yl)-xanthine
(15) 1-[(3-cyano-pyridin-4-yl)methyl]-3-phenyl-7-(2-butyn-1-yl)-8-((R)-3-amino-piperidin-1-yl)-xanthine
(16) 1-[(2-cyano-pyridin-3-yl)methyl]-3-phenyl-7-(2-butyn-1-yl)-8-((R)-3-amino-piperidin-1-yl)-xanthine
(17) 1-[(2-cyano-pyridin-4-yl)methyl]-3-phenyl-7-(2-butyn-1-yl)-8-((R)-3-amino-piperidin-1-yl)-xanthine
(18) 1-[(5-cyano-pyridin-3-yl)methyl]-3-phenyl-7-(2-butyn-1-yl)-8-((R)-3-amino-piperidin-1-yl)-xanthine
(19) 1-[(6-cyano-pyridin-3-yl)methyl]-3-phenyl-7-(2-butyn-1-yl)-8-((R)-3-amino-piperidin-1-yl)-xanthine
(20) 1-(2-cyano-4-methoxy-benzyl)-3-phenyl-7-(2-butyn-1-yl)-8-((R)-3-amino-piperidin-1-yl)-xanthine
(21) 1-(2-cyano-5-methoxy-benzyl)-3-phenyl-7-(2-butyn-1-yl)-8-((R)-3-amino-piperidin-1-yl)-xanthine
(22) 1-[(3-cyano-quinolin-2-yl)methyl]-3-phenyl-7-(2-butyn-1-yl)-8-((R)-3-amino-piperidin-1-yl)-xanthine
(23) 1-(2-methoxy-benzyl)-3-phenyl-7-(2-butyn-1-yl)-8-((R)-3-amino-piperidin-1-yl)-xanthine
(24) 1-(2-trifluoromethyl-benzyl)-3-phenyl-7-(2-butyn-1-yl)-8-((R)-3-amino-piperid in-1-yl)-xanthine
(25) 1-[(quinoxalin-6-yl)methyl]-3-phenyl-7-(2-butyn-1-yl)-8-((R)-3-amino-piperidin-1-yl)-xanthine
(26) 1-(3-fluoro-benzyl)-3-phenyl-7-(2-butyn-1-yl)-8-((R)-3-amino-piperidin-1-yl)-xanthine
(27) 1-(4-fluoro-benzyl)-3-phenyl-7-(2-butyn-1-yl)-8-((R)-3-amino-piperidin-1-yl)-xanthine
(28) 1-(3-chlorobenzyl)-3-phenyl-7-(2-butyn-1-yl)-8-((R)-3-amino-piperidin-1-yl)-xanthine
(29) 1-(4-chlorobenzyl)-3-phenyl-7-(2-butyn-1-yl)-8-((R)-3-amino-piperidin-1-yl)-xanthine
(30) 1-[3-(trifluoromethyl)-benzyl]-3-phenyl-7-(2-butyn-1-yl)-8-((R)-3-amino-piperidin-1-yl)-xanthine
(31) 1-[4-(trifluoromethyl)-benzyl]-3-phenyl-7-(2-butyn-1-yl)-8-((R)-3-amino-piperidin-1-yl)-xanthine
(32) 1-(3-methoxy-benzyl)-3-phenyl-7-(2-butyn-1-yl)-8-((R)-3-amino-piperidin-1-yl)-xanthine
(33) 1-(4-methoxy-benzyl)-3-phenyl-7-(2-butyn-1-yl)-8-((R)-3-amino-piperidin-1-yl)-xanthine
(34) 1-[2-(difluoromethoxy)-benzyl]-3-phenyl-7-(2-butyn-1-yl)-8-((R)-3-amino-piperidin-1-yl)-xanthine
(35) 1-[3-(difluoromethoxy)-benzyl]-3-phenyl-7-(2-butyn-1-yl)-8-((R)-3-amino-piperidin-1-yl)-xanthine
(36) 1-[4-(difluoromethoxy)-benzyl]-3-phenyl-7-(2-butyn-1-yl)-8-((R)-3-amino-piperidin-1-yl)-xanthine
(37) 1-[2-(trifluoromethoxy)-benzyl]-3-phenyl-7-(2-butyn-1-yl)-8-((R)-3-amino-piperidin-1-yl)-xanthine
(38) 1-[3-(trifluoromethoxy)-benzyl]-3-phenyl-7-(2-butyn-1-yl)-8-((R)-3-amino-piperidin-1-yl)-xanthine
(39) 1-[4-(trifluoromethoxy)-benzyl]-3-phenyl-7-(2-butyn-1-yl)-8-((R)-3-amino-piperidin-1-yl)-xanthine
(40) 1-(2-cyano-3-methoxy-benzyl)-3-phenyl-7-(2-butyn-1-yl)-8-((R)-3-amino-piperidin-1-yl)-xanthine

EXAMPLE 2

Coated Tablets Containing 75 mg of Active Substance
1 tablet core contains:

| | |
|---|---|
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:
The active substance is mixed with calcium phosphate, corn starch, polyvinylpyrrolidone, hydroxypropylmethylcellulose and half the specified amount of magnesium stearate. Blanks about 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape.

| | |
|---|---|
| Weight of core: | 230 mg |
| Die: | 9 mm, convex |

The tablet cores thus produced are coated with a film consisting essentially of hydroxypropylmethylcellulose. The finished film-coated tablets are polished with beeswax.

| | |
|---|---|
| Weight of coated tablet: | 245 mg. |

EXAMPLE 3

Tablets Containing 100 mg of Active Substance

Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Preparation:
The active substance, lactose and starch, are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets.

| | |
|---|---|
| Weight of tablet: | 220 mg |
| Diameter: | 10 mm, biplanar, facetted on both sides and notched on one side. |

EXAMPLE 4

Tablets Containing 150 mg of Active Substance

Composition:

1 tablet contains:

| | |
|---|---|
| active substance | 150.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch, and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture.

| | |
|---|---|
| Weight of tablet: | 300 mg |
| Die: | 10 mm, flat |

EXAMPLE 5

Hard Gelatin Capsules Containing 150 mg of Active Substance 1 capsule contains:

| | |
|---|---|
| active substance | 150.0 mg |
| corn starch (dried) | approx. 180.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm, and homogeneously mixed using a suitable apparatus. The finished mixture is packed into size 1 hard gelatin capsules.

| | |
|---|---|
| Capsule filling: | approx. 320 mg |
| Capsule shell: | size 1 hard gelatin capsule. |

EXAMPLE 6

Suppositories Containing 150 mg of Active Substance 1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled moulds.

EXAMPLE 7

Suspension Containing 50 mg of Active Substance 100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavoring | 0.30 g |
| dist. water | ad 100.00 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution, and the flavoring have been added and dissolved, the suspension is evacuated with stirring to eliminate air.

5 ml of suspension contains 50 mg of active substance.

EXAMPLE 8

Ampoules Containing 10 mg Active Substance

Composition:

| | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile, and transferred into 2 ml ampoules.

EXAMPLE 9

Ampoules Containing 50 mg of Active Substance
Composition:

| active substance | 50.0 mg |
| --- | --- |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile, and transferred into 10 ml ampoules.

We claim:

1. A compound of general formula I

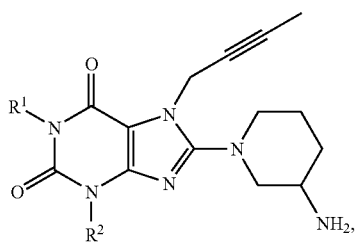

(I)

wherein $R^1$ is selected from the group consisting of: benzyl, 2-fluorobenzyl, 3-fluorobenzyl, 4-fluorobenzyl, 2-chlorobenzyl, 3-chlorobenzyl, 4-chlorobenzyl, 2-(trifluoromethyl)-benzyl, 3-(trifluoromethyl)-benzyl, 4-(trifluoromethyl)-benzyl, 2-methoxybenzyl, 3-methoxybenzyl, 4-methoxybenzyl, 2-(difluoromethoxy)-benzyl, 3-(difluoromethoxy)-benzyl, 4-(difluoromethoxy)-benzyl, 2-(trifluoromethoxy)-benzyl, 3-(trifluoromethoxy)-benzyl, 4-(trifluoromethoxy)-benzyl, a 2-cyanobenzyl, 3-cyanobenzyl, 4-cyanobenzyl, 2-cyano-3-methoxy-benzyl, 2-cyano-4-methoxy-benzyl, 2-cyano-5-methoxy-benzyl, 2-cyano-4-fluoro-benzyl, 2-cyano-5-fluoro-benzyl, 2-cyano-6-fluoro-benzyl, 2-(3-methoxy-phenyl)-2-oxo-ethyl, 2-(3-methyl-2-oxo-2,3-dihydro-benzoxazol-4-yl)-2-oxo-ethyl, (pyridin-2-yl)methyl, (3-cyanopyridin-2-yl)methyl, (6-cyanopyridin-2-yl)methyl, (5-cyano-pyridin-2-yl)methyl, (4-cyano-pyridin-2-yl)methyl, (4-cyano-pyridin-3-yl)methyl, (3-cyano-pyridin-4-yl)methyl, (2-cyano-pyridin-3-yl)methyl, (2-cyano-pyridin-4-yl)methyl, (5-cyano-pyridin-3-yl)methyl, (6-cyano-pyridin-3-yl)methyl, (3-cyano-quinolin-2-yl)methyl, (1-cyano-isoquinolin-3-yl)methyl, (4-cyano-isoquinolin-1-yl)methyl, (4-methyl-quinazolin-2-yl)methyl, (quinoxalin-6-yl)methyl, (2,3-dimethyl-quinoxalin-6-yl)methyl, and ([1,5]naphthyridin-2-yl)methyl; and $R^2$ is cyclopropyl or phenyl, the tautomers and the salts thereof.

2. The compound of claim 1, selected from the group consisting of:

1-[2-(3-Methyl-2-oxo-2,3-dihydro-benzoxazol-4-yl)-2-oxo-ethyl]-3-cyclopropyl-7-(2-butyn-1-yl)-8-((R)-3-amino-piperidin-1-yl)-xanthine; 1-[(4-methyl-quinazolin-2-yl)methyl]-3-cyclopropyl-7-(2-butyn-1-yl)-8-((R)-3-amino-piperidin-1-yl)-xanthine; 1-[2-(3-methoxy-phenyl)-2-oxo-ethyl]-3-cyclopropyl-7-(2-butyn-1-yl)-8-((R)-3-amino-piperidin-1-yl)-xanthine; 1-[(4-cyano-isoquinolin-1-yl)methyl]-3-cyclopropyl-7-(2-butyn-1-yl)-8-((R)-3-amino-piperidin-1-yl)-xanthine; 1-[(1-cyano-isoquinolin-3-yl)methyl]-3-cyclopropyl-7-(2-butyn-1-yl)-8-((R)-3-amino-piperidin-1-yl)-xanthine; 1-[([1,5]naphthyridin-2-yl)methyl]-3-cyclopropyl-7-(2-butyn-1-yl)-8-((R)-3-amino-piperidin-1-yl)-xanthine; 1-[(2,3-dimethyl-quinoxalin-6-yl)methyl]-3-cyclopropyl-7-(2-butyn-1-yl)-8-((R)-3-amino-piperidin-1-yl)-xanthine; 1-[(4-methyl-quinazolin-2-yl)methyl]-3-phenyl-7-(2-butyn-1-yl)-8-((R)-3-amino-piperidin-1-yl)-xanthine; 1-[2-(3-methyl-2-oxo-2,3-dihydro-benzoxazol-4-yl)-2-oxo-ethyl]-3-phenyl-7-(2-butyn-1-yl)-8-((R)-3-amino-piperidin-1-yl)-xanthine; 1-[2-(3-methoxy-phenyl)-2-oxo-ethyl]-3-phenyl-7-(2-butyn-1-yl)-8-((R)-3-amino-piperidin-1-yl)-xanthine; 1-[(4-cyano-isoquinolin-1-yl)methyl]-3-phenyl-7-(2-butyn-1-yl)-8-((R)-3-amino-piperidin-1-yl)-xanthine; 1-[(1-cyano-isoquinolin-3-yl)methyl]-3-phenyl-7-(2-butyn-1-yl)-8-((R)-3-amino-piperidin-1-yl)-xanthine; 1-[([1,5]naphthyridin-2-yl)methyl]-3-phenyl-7-(2-butyn-1-yl)-8-((R)-3-amino-piperidin-1-yl)-xanthine; 1-[(2,3-dimethyl-quinoxalin-6-yl)methyl]-3-phenyl-7-(2-butyn-1-yl)-8-((R)-3-amino-piperidin-1-yl)-xanthine; 1-(2-cyano-benzyl)-3-phenyl-7-(2-butyn-1-yl)-8-((R)-3-amino-piperidin-1-yl)-xanthine; 1-(2-cyano-benzyl)-3-cyclopropyl-7-(2-butyn-1-yl)-8-((R)-3-amino-piperidin-1-yl)-xanthine; 1-(2-cyano-4-fluoro-benzyl)-3-phenyl-7-(2-butyn-1-yl)-8-((R)-3-amino-piperidin-1-yl)-xanthine; 1-(2-cyano-5-fluoro-benzyl)-3-phenyl-7-(2-butyn-1-yl)-8-((R)-3-amino-piperidin-1-yl)-xanthine; 1-(2-cyano-6-fluoro-benzyl)-3-phenyl-7-(2-butyn-1-yl)-8-((R)-3-amino-piperidin-1-yl)-xanthine; 1-(3-cyanobenzyl)-3-phenyl-7-(2-butyn-1-yl)-8-((R)-3-amino-piperidin-1-yl)-xanthine; 1-(4-cyanobenzyl)-3-phenyl-7-(2-butyn-1-yl)-8-((R)-3-amino-piperidin-1-yl)-xanthine; 1-benzyl-3-phenyl-7-(2-butyn-1-yl)-8-((R)-3-amino-piperidin-1-yl)-xanthine; 1-[(pyridin-2-yl)methyl]-3-phenyl-7-(2-butyn-1-yl)-8-((R)-3-amino-piperidin-1-yl)-xanthine; 1-(2-chlorobenzyl)-3-phenyl-7-(2-butyn-1-yl)-8-((R)-3-amino-piperidin-1-yl)-xanthine; 1-(2-fluoro-benzyl)-3-phenyl-7-(2-butyn-1-yl)-8-((R)-3-amino-piperidin-1-yl)-xanthine; 1-[(3-cyano-pyridin-2-yl)methyl]-3-phenyl-7-(2-butyn-1-yl)-8-((R)-3-amino-piperidin-1-yl)-xanthine; 1-[(6-cyano-pyridin-2-yl)methyl]-3-phenyl-7-(2-butyn-1-yl)-8-((R)-3-amino-piperidin-1-yl)-xanthine; 1-[(5-cyano-pyridin-2-yl)methyl]-3-phenyl-7-(2-butyn-1-yl)-8-((R)-3-amino-piperidin-1-yl)-xanthine; 1-1-[(4-cyano-pyridin-2-yl)methyl]-3-phenyl-7-(2-butyn-1-yl)-8-((R)-3-amino-piperidin-1-yl)-xanthine; 1-[(4-cyano-pyridin-3-yl)methyl]-3-phenyl-7-(2-butyn-1-yl)-8-((R)-3-amino-piperidin-1-yl)-xanthine; 1-[(3-cyano-pyridin-4-yl)methyl]-3-phenyl-7-(2-butyn-1-yl)-8-((R)-3-amino-piperidin-1-yl)-xanthine; 1-[(2-cyano-pyridin-3-yl)methyl]-3-phenyl-7-(2-butyn-1-yl)-8-

((R)-3-amino-piperidin-1-yl)-xanthine; 1-[(2-cyano-pyridin-4-yl)methyl]-3-phenyl-7-(2-butyn-1-yl)-8-((R)-3-amino-piperidin-1-yl)-xanthine; 1-[(5-cyano-pyridin-3-yl)methyl]-3-phenyl-7-(2-butyn-1-yl)-8-((R)-3-amino-piperidin-1-yl)-xanthine; 1-[(6-cyano-pyridin-3-yl)methyl]-3-phenyl-7-(2-butyn-1-yl)-8-((R)-3-amino-piperidin-1-yl)-xanthine; 1-(2-cyano-4-methoxy-benzyl)-3-phenyl-7-(2-butyn-1-yl)-8-((R)-3-amino-piperidin-1-yl)-xanthine; 1-(2-cyano-5-methoxy-benzyl)-3-phenyl-7-(2-butyn-1-yl)-8-((R)-3-amino-piperidin-1-yl)-xanthine; 1-[1(3-cyano-quinolin-2-yl)methyl]-3-phenyl-7-(2-butyn-1-yl)-8-((R)-3-amino-piperidin-1-yl)-xanthine; 1-(2-methoxy-benzyl)-3-phenyl-7-(2-butyn-1-yl)-8-((R)-3-amino-piperidin-1-yl)-xanthine; 1-(2-trifluoromethyl-benzyl)-3-phenyl-7-(2-butyn-1-yl)-8-((R)-3-amino-piperidin-1-yl)-xanthine; 1-[(quinoxalin-6-yl)methyl]-3-phenyl-7-(2-butyn-1-yl)-8-((R)-3-amino-piperidin-1-yl)-xanthine; 1-(3-fluoro-benzyl)-3-phenyl-7-(2-butyn-1-yl)-8-((R)-3-amino-piperidin-1-yl)-xanthine; 1-(4-fluoro-benzyl)-3-phenyl-7-(2-butyn-1-yl)-8-((R)-3-amino-piperidin-1-yl)-xanthine; 1-(3-chlorobenzyl)-3-phenyl-7-(2-butyn-1-yl)-8-((R)-3-amino-piperidin-1-yl)-xanthine; 1-(4-chlorobenzyl)-3-phenyl-7-(2-butyn-1-yl)-8-((R)-3-amino-piperidin-1-yl)-xanthine; 1-[3-(trifluoromethyl)-benzyl]-3-phenyl-7-(2-butyn-1-yl)-8-((R)-3-amino-piperidin-1-yl)-xanthine; 1-[4-(trifluoromethyl)-benzyl]-3-phenyl-7-(2-butyn-1-yl)-8-((R)-3-amino-piperidin-1-yl)-xanthine; 1-(3-methoxy-benzyl)-3-phenyl-7-(2-butyn-1-yl)-8-((R)-3-amino-piperidin-1-yl)-xanthine; 1-(4-methoxy-benzyl)-3-phenyl-7-(2-butyn-1-yl)-8-((R)-3-amino-piperidin-1-yl)-xanthine; 1-[2-(difluoromethoxy)-benzyl]-3-phenyl-7-(2-butyn-1-yl)-8-((R)-3-amino-piperidin-1-yl)-xanthine; 1-[3-(difluoromethoxy)-benzyl]-3-phenyl-7-(2-butyn-1-yl)-8-((R)-3-amino-piperidin-1-yl)-xanthine;
1-[4-(difluoromethoxy)-benzyl]-3-phenyl-7-(2-butyn-1-yl)-8-((R)-3-amino-piperidin-1-yl)-xanthine; 1-[2-(trifluoromethoxy)-benzyl]-3-phenyl-7-(2-butyn-1-yl)-8-((R)-3-amino-piperidin-1-yl)-xanthine; 1-[3-(trifluoromethoxy)-benzyl]-3-phenyl-7-(2-butyn-1-yl)-8-((R)-3-amino-piperidin-1-yl)-xanthine; 1-[4-(trifluoromethoxy)-benzyl]-3-phenyl-7-(2-butyn-1-yl)-8-((R)-3-amino-piperidin-1-yl)-xanthine; and 1-(2-cyano-3-methoxy-benzyl)-3-phenyl-7-(2-butyn-1-yl)-8-((R)-3-amino-piperidin-1-yl)-xanthine.

3. The compound according to claim 1, in the form of a physiologically acceptable salt with an inorganic or organic acid.

4. A pharmaceutical composition comprising a compound according to claim 1, or a physiologically acceptable salt thereof, with one or more inert carriers or diluents.

5. A process for preparing the compound according to claim 1, the process comprising:

(a) reacting a compound of general formula II

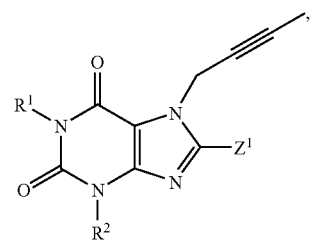

wherein
$R^1$ and $R^2$ are defined as in claim 1, and
$Z^1$ is a leaving group,
with 3-aminopiperidine, the enantiomers, or the salts thereof;

or (b) deprotecting a compound of general formula III

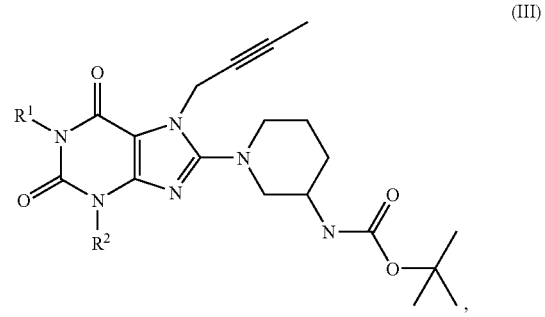

wherein $R^1$ and $R^2$ are defined as in claim 1.

6. A method for preventing type II diabetes mellitus or obesity, the method comprising the step of administering to a patient a pharmaceutically effective amount of the compound according to claim 1.

7. The process of claim 5, wherein $Z^1$ is a halogen atom, or a mercapto, methanesulphonyl or methanesulphonyloxy group.

8. The compound according to claim 1, wherein $R^2$ is cyclopropyl.

9. The compound according to claim 1, wherein $R^2$ is phenyl.

* * * * *

UNITED STATES PATENT AND TRADEMARK OFFICE
CERTIFICATE OF CORRECTION

PATENT NO. : 7,645,763 B2  Page 1 of 1
APPLICATION NO. : 11/062518
DATED : January 12, 2010
INVENTOR(S) : Himmelsbach et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1041 days.

Signed and Sealed this

Sixteenth Day of November, 2010

David J. Kappos
*Director of the United States Patent and Trademark Office*